United States Patent [19]

Solar et al.

[11] Patent Number: 4,976,690
[45] Date of Patent: Dec. 11, 1990

[54] VARIABLE STIFFNESS ANGIOPLASTY CATHETER

[75] Inventors: Ronald J. Solar, Minnetonka; Jonathan Kagan, Minneapolis, both of Minn.

[73] Assignee: SciMed Life Systems, Inc., Maple Grove, Minn.

[21] Appl. No.: 497,812

[22] Filed: Mar. 22, 1990

Related U.S. Application Data

[63] Continuation of Ser. No. 394,303, Aug. 10, 1989, abandoned, which is a continuation of Ser. No. 274,738, Nov. 14, 1988, abandoned, which is a continuation of Ser. No. 135,559, Dec. 17, 1987, abandoned, which is a continuation of Ser. No. 766,763, Aug. 16, 1985, abandoned.

[51] Int. Cl.$^5$ ............................................. A61M 29/00
[52] U.S. Cl. ......................................... 604/96; 606/194
[58] Field of Search ................................. 604/95–103, 604/280; 128/325, 344, 348

[56] References Cited

U.S. PATENT DOCUMENTS

| | | |
|---|---|---|
| 3,435,826 | 4/1969 | Fogarty . |
| 3,605,725 | 9/1971 | Benton ............................. 128/348 X |
| 3,789,841 | 2/1974 | Antoshkiw . |
| 3,890,976 | 6/1975 | Bazell et al. ..................... 128/348 X |
| 3,995,623 | 12/1976 | Blake et al. . |
| 4,003,369 | 1/1977 | Heilman et al. . |
| 4,024,873 | 5/1977 | Antoshkiw et al. ............. 128/348 X |
| 4,029,104 | 6/1977 | Kerber .................................. 128/348 |
| 4,299,226 | 11/1981 | Banka . |
| 4,385,635 | 5/1983 | Ruiz . |
| 4,402,307 | 9/1983 | Hanson et al. ................... 128/344 X |
| 4,413,989 | 11/1983 | Schjeldahl et al. . |
| 4,445,892 | 5/1984 | Hussein et al. ....................... 604/101 |
| 4,464,176 | 8/1984 | Wijayarathna . |
| 4,516,972 | 5/1985 | Samson . |
| 4,531,943 | 7/1985 | Van Tassel et al. .............. 604/96 X |
| 4,545,390 | 10/1985 | Leary ................................ 604/96 X |
| 4,553,959 | 11/1985 | Hickey et al. ........................ 604/96 |
| 4,582,181 | 4/1986 | Samson . |
| 4,616,653 | 10/1986 | Samson et al. . |
| 4,619,274 | 10/1986 | Morrison . |
| 4,646,742 | 3/1987 | Packard et al. ................. 604/102 X |
| 4,723,936 | 2/1988 | Buchbinder et al. ................. 604/95 |
| 4,844,579 | 12/1989 | Engelson . |

FOREIGN PATENT DOCUMENTS 0102685 of 0000 European Pat. Off. .
0213748 11/1987 European Pat. Off. .

Primary Examiner—John D. Yasko
Attorney, Agent, or Firm—Willian Brinks Olds Hofer Gilson & Lione

[57] ABSTRACT

An improved vascular catheter for angioplasty providing a variable stiffness lengthwise of the catheter. A relatively stiff shaft portion is provided for transmitting the necessary axial forces for advancing the catheter along a guide wire through a series of sharp bend to the arterial branch for dilatation, and a more flexible waist portion connects from the shaft to the balloon and tip portion. This allows the tip and balloon portions to follow sharply bending turns in the guide wire without the shaft portion tending to push the tip beyond a branch or dislodge the guide wire. A set of such catheters may be provided for a surgical procedure, having varying lengths of the waist portion according to the circumstances of the case. If a sharp turn is encountered that cannot be tracked, the catheter can be withdrawn leaving the guide wire in place, and another catheter of the set having a longer waist portion can be inserted to successfully follow the turn.

32 Claims, 3 Drawing Sheets

VARIABLE STIFFNESS ANGIOPLASTY CATHETER

This application is a continuation of application Ser. No. 07/394,303, filed Aug. 10, 1989, abandoned, which is a continuation of Ser. No. 07/274,736, filed Nov. 14, 1988, abandoned, which is a continuation of Ser. No. 07/135,559, filed Dec. 17, 1987, abandoned, which is a continuation of Ser. No. 06/766,763, filed Aug. 16, 1985.

FIELD OF THE INVENTION

This invention relates to vascular catheters for use in percutaneous transluminal angioplasty procedures. In particular, the invention is especially adapted to treatment of coronary arteries with catheters introduced percutaneously remote from the heart and advanced along a guide wire to a coronary artery for dilating a stenosis therein.

BACKGROUND OF THE INVENTION

Angioplasty has become an accepted and rapidly expanding method for the treatment of certain types of vascular disease. In percutaneous transluminal angioplasty, a guide wire is introduced percutaneously into the patient's vascular system and advanced and steered to the site of the stenosis. A dilation catheter is then advanced over the guide wire until it is positioned at the stenosis site so that it can be inflated to dilatate the artery and reestablish a more adequate blood flow path therethrough.

Such techniques are especially important in the treatment of coronary artery diseases by percutaneous transluminal coronary angioplasty. In coronary applications, guide catheters, guide wires and angioplasty catheters have been specially developed for maneuvering through numerous arterial branches and into the particular coronary artery branch where treatment is desired. Because of the many branches which must be successfully negotiated and the convoluted, tortuous path which must be followed by the catheter, numerous specialized instruments have been developed for this purpose, with the result that an increasingly large number of cases can be successfully treated. However, certain problems still can be encountered in the positioning of the angioplasty catheter, especially in the final few tight branches an turns leading to a stenosis site in a coronary artery. The problem can occur after a guide wire has successfully been advanced into position and while the dilatation catheter is being advanced over the guide wire. When encountering a sharp turn to a smaller artery, it is possible that the distal end of the dilatation catheter may be too stiff to make the small radius turn. This can cause great difficulty in trying to manipulate and maneuver the catheter around the turn, and in extreme cases can result in the catheter actually advancing down the wrong branch and pulling the guide wire out of the intended branch.

Prior art catheters tend to have a relatively stiff shaft which transitions at the beginning of the balloon to a lower stiffness. This means that the flexible distal portion of a prior art catheter consists only of the relatively small tip and the balloon, with the stiffer shaft starting immediately adjacent the balloon. This may not provide sufficient flexibility to permit the catheter to follow sharp bends, and may result in the stiff shaft pushing the balloon past the branch and even pulling the guide wire out of the branch.

An alternate construction in the prior art uses a central lumen defining tube, and an outer, relatively flexible tube which forms the shaft and which has the balloon formed integrally therewith at the end. While this type of construction provides great flexibility for following sharp bends, after a number of such bends have been encountered, the shaft is too soft to transmit sufficient axial force without buckling, and it becomes impossible to advance the catheter any farther.

SUMMARY OF THE INVENTION

To overcome these and other problems, the present invention provides a variable stiffness, or variable softness catheter, which has a tip area that is soft enough to follow sharp tortuous bends of a guide wire without dislodging it, and which has a shaft portion which is stiff enough to provide the necessary axial force transmission so that the catheter can be advanced even after following a great number of bends. This is accomplished in the present invention by providing a catheter construction which has a shaft portion which is stiff enough to transmit axial forces needed to advance the catheter, a relatively flexible tip and balloon portion, and an intermediate portion, referred to herein as a "waist" portion between the shaft and the balloon, which has less stiffness than the shaft and permits a greater degree of flexibility of the whole tip area for following sharp turns as the catheter is being advanced.

According to another aspect of the invention, a set of matched catheters is provided for use in an angioplasty procedure, with individual catheters of the set having different lengths of the less-stiff waist portion. This allows the physician to match the catheter to the particular procedure at hand, and if a sharp bend is encountered which the tip cannot follow without tending to "pull" the wire from the intended branch, as referred to above, then it is a simple matter to withdraw the catheter, leaving the guide wire in place, and reintroduce another catheter from the set with a longer waist, so that the sharp bend can be accomplished.

DETAILED DESCRIPTION OF THE PREFERRED EMBODIMENTS

Figure 1:
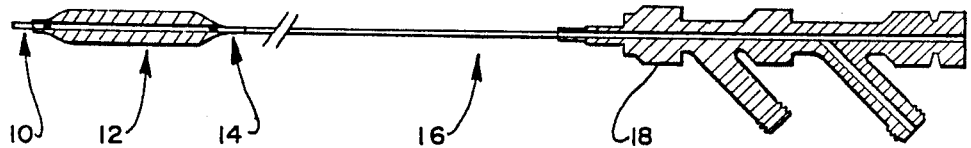
FIG. 1 is a sectional view of a catheter and hub assembly in accordance with one embodiment of the invention.

A preferred embodiment of the present invention is shown generally in FIG. 1, and the tip portion thereof is shown in greater detail in enlarged sectional views 2A and 2B which are substantially identical except for a difference in the length of the intermediate or waist portion.

The catheter generally has a tip area 10, an inflatable balloon area 12, intermediate or waist portion 14, and a shaft portion 16 which extends all the way up to the proximal end of the catheter and includes an appropriate fitting or hub assembly 18 for connection to the apparatus for applying dilatation pressure, and for administering medication and sensing arterial pressure as is generally known in the art.

In construction of the catheter, a hollow inner tube 21 is provided which runs the entire length of the catheter, and which defines the central lumen 22. Inner tube 21 may be made of any number of materials, and in the preferred embodiment is made of a blend of high and low density polyethylene in order to give desired mechanical properties. Central lumen 22 receives the guide wire (not shown) in use so that the catheter can be advanced over the guide wire to the site of the stenosis.

The shaft portion 16 comprises a hollow outer tube 25 of sufficient inside diameter to receive inner tube 21 and to define an annular lumen 26 between the inside diameter of tube 25 and the outside diameter of tube 21. This annular lumen is used for transmitting pressure from pressure control apparatus outside the patient to the dilatation balloon. Outer tube 25 can be made from any suitable material, for example a blend of high and low density polyethylene selected to give desired mechanical properties. Tube 25 should be stiff enough mechanically to provide axial pushing forces so that the catheter can be advanced over the guide wire without buckling, yet flexible enough to follow the typical multiple-turn tortuous path from the site of introduction in the body to the arterial branch where the dilatation will take place. However, some of the needed flexibility is provided in the tip, balloon, and waist as described below. At its distal end 27 outer tube 25 is necked down slightly so as to receive tubing section 30, which fits over the necked down portion and is secured thereto by any suitable method, for example adhesive bonding, heat fusion or shrink fitting. In this manner the joint is made without a bump or protrusion on the outside of the catheter which would interfere with movement of the catheter through arterial branches.

Tubing section 30 is used to form the waist portion 14 and the balloon portion 12. Section 30 is made in the preferred embodiment of polyolefin copolymer formed in a tube section of sufficient diameter to substantially match outer tube 25 and be positioned over inner tube 21, while still keeping annular lumen 26 open. The balloon section 12 and the waist section 14 are formed integrally of the same tubing section 30, but the dilatation balloon 12 is expanded as is generally known to provide the inflatable balloon area for dilatation. This balloon can be formed in any of several ways as is generally known, for example by blow molding, or blowing while applying heat.

The distal end 32 of tubing section 30, beyond balloon 12, necks down to substantially the diameter of inner tube 21 and is secured thereto for example by adhesive bonding, heat fusion or heat shrinking. A section of inner tube 21 extends beyond distal end 32 to form the flexible tip portion. A pair of radiopaque markers 34 are bonded onto inner tube 21 at the ends of balloon section 12 for use in fluoroscopic observation of balloon position the distance between the ends of balloon section 12 is labeled in FIG. 2A as L.

Figure 2A:
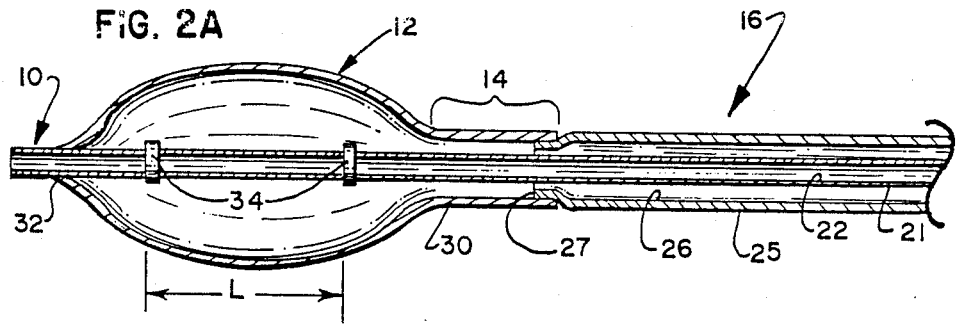
FIG. 2A is an enlarged sectional view of the tip portion of a catheter according to the present invention.
Figure 2B:
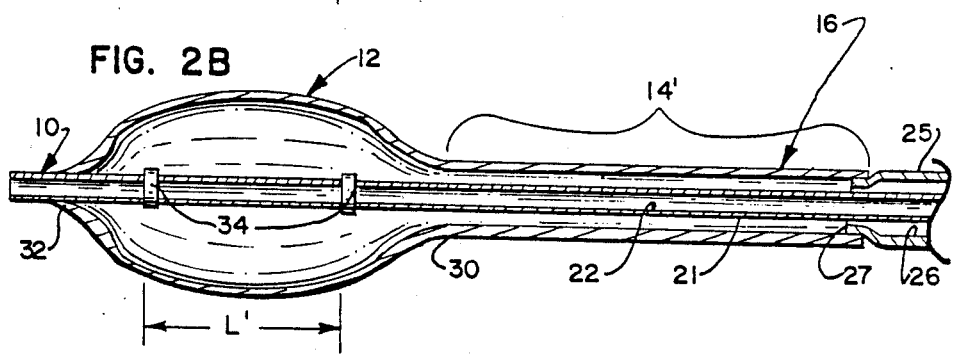
FIG. 2B is a view similar to FIG. 2A but showing a catheter having a different length of the waist portion.

The catheters of FIGS. 2A and 2B are substantially identical, except that the waist portion 14' of FIG. 2B is intentionally made longer than the waist portion 14 of FIG. 2A. In practice a number of models of the catheter can be made having a number of steps or gradations of length of the waist 14 for different applications. As illustrated in FIG. 2A, the length of the waist 14 is at least one-half of the balloon length L. Further, as shown in FIG. 2B, the length of the waist 14' may be at least as long as one balloon length L or greater.

It will be appreciated that the catheter provided by the present invention provides a variable stiffness or softness along the length of the catheter. The tip 10 may be the softest, as it consists essentially of only the inner tube, and balloon section 12 may also be relatively soft. On the other hand, shaft section 16 will be relatively stiff since it includes outer tube 25. The waist portion 14 will be less stiff than shaft portion 16, since outer tube 25 does not extend into the waist portion 14, and tubing section 30 is less stiff than outer tube 25.

Thus, the entire distal end, which includes tip 10, balloon 12 and waist 14, is soft and flexible enough to follow sharp bends in the guide wire, while the shaft 16 provides sufficient mechanical stiffness to transmit axial pushing forces without buckling. The waist 14 provides added length to keep the stiff part of shaft 16 away from the zone in which the distal portion is attempting to follow a sharply-turning guide wire, so that pushing on the shaft 16 will not cause dislodging of the guide wire as in the prior art.

Figure 3A:
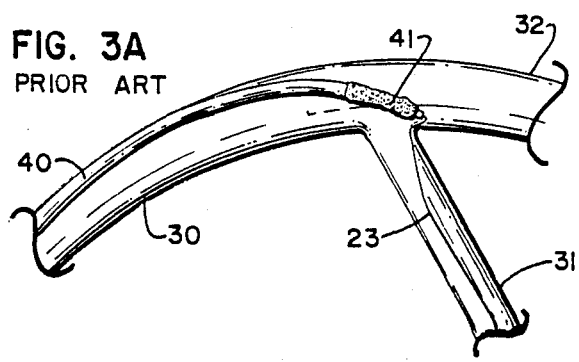
FIG. 3A is a diagrammatic view illustrating the problem encountered in the prior art of attempting to maneuver a stiff catheter into a sharp turn to a branch of an artery.

The problem existing in the prior art is illustrated in FIG. 3A, which diagrammatically shows a catheter which consists of a shaft portion 40 and a balloon portion 41 being advanced over a guide wire 23 which is previously positioned in an arterial branch 31 of an artery 30. Due to the sharp bend of the guide wire from artery 30 to branch 31, and due to stiffness of shaft 40 which extends up to the softer tip 41, the catheter is unable to make the sharp turn and further axial pushing on the catheter will push the tip thereof down straight branch 32, and may actually pull guide wire 23 from out of branch 31 which of course causes great difficulty.

Figure 3B:
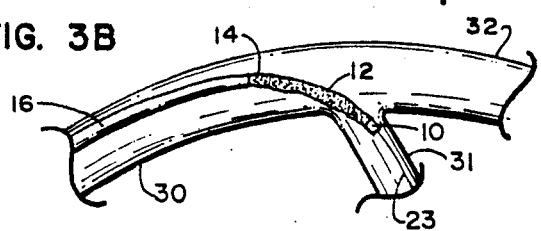
FIG. 3B is a diagrammatic view similar to FIG. 2A illustrating the operation of a catheter of the present invention in accomplishing the sharp turn.

The similar maneuver is shown diagrammatically in FIG. 3B, but this time using a catheter according to the present invention, which has a relatively stiff shaft 16, and a less stiff waist portion 14 between the shaft 16 and the balloon portion 12. Because of the more flexible waist portion of the distal end including top 11, balloon 12 and waist 14 is able to make the sharp bend and follow guide wire 23 in branch 31. By the time that the stiffer shaft portion 16 reaches the branch, the balloon and waist portion will already be well into the branch, so the shaft will be likely to follow without dislodging the catheter or guide wire. Alternatively, if the turn to branch 31 is extremely sharp, and depending on the location of the stenosis at which the balloon 12 must be positioned, the catheter may be withdrawn while leaving guide wire 23 in place, while another catheter according to the present invention with an even longer waist 14 can be inserted, to provide a longer flexible portion or possibly to reach the stenosis without shaft 16 having to make the sharp bend.

Alternate methods of construction for catheters according to the present invention are shown in FIGS. 4a and 4b, 5a and 5b, and 6a and 6b. In each case, the catheters have tip portions 10, balloon portions 12, a waist or intermediate portion 14 or 14', and a shaft portion 16. It will be understood that in each case the catheter shaft would extend for connection to a hub assembly or fitting 18 as suggested in FIG. 1 and as generally shown in the art for use in applying the dilatation pressure, administering medication, and sensing arterial pressure.

Figure 4A:
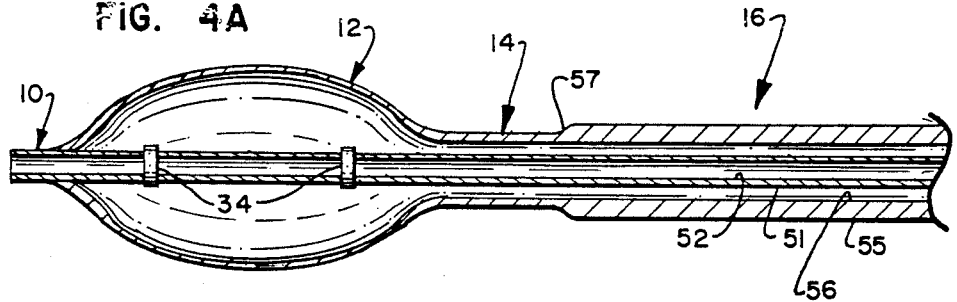
FIGS. 4A and 4B are enlarged sectional views of the tip portions of short and long waist catheters according to an alternative embodiment of the invention.
Figure 4B:
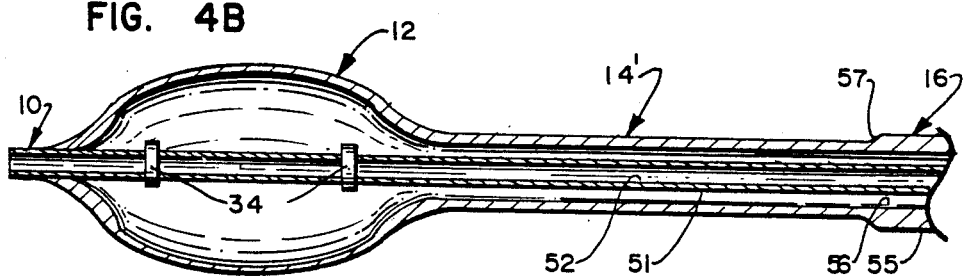

In the embodiment of FIGS. 4A and 4B the balloon section 12 is formed integrally with the waist portion 14 and the other tubular member of the shaft 16, with the thickness thereof being stepped or decreased in the waist and balloon area to provide greater flexibility. The catheters of FIGS. 4A and 4B each include a hollow inner tubular member 51 which defines central lumen 52 which extends through the catheter for receiving the guide wire as the catheter is being advanced. At its distal end, inner tube 51 forms the tip portion 10. Radiopaque markers 34 are bonded to the tube 51 in the balloon area 12 as is qenerally known. The shaft portion 16 comprises a hollow outer tube 55 which has a large enough inside diameter to receive inner tube 51 and to define an annular lumen 56 between the inside wall of tube 51. As in the case of the previous embodiment, the annular lumen is used for supplying dilatation pressure to the balloon. The material and wall thickness for tube 55 is chosen to give sufficient axial mechanical rigidity as described previously, so as to withstand and transmit axial pushing forces while the catheter is being advanced through the arteries.

The balloon and waist portions are formed integrally with tube 55, by stepping or necking down the wall thickness of tube 55 at the zone indicated by reference number 57, which in effect defines the end of the shaft portion 16 and the beginning of the waist portion 14. The balloon portion 12 is formed in the thin walled distal end of tube 55 by known techniques previously described, and the end thereof is bonded to the inner tube to seal off the balloon. Since waist portion 14 has a thinner sectioned wall than the main portion of tube 55 which defines shaft 16, it will have less stiffness and greater flexibility to permit it to follow turns as the catheter is advanced.

FIG. 4B is similar, except that the length of waist portion 14' is longer to provide even greater flexibility for following sharply turning branches, as described above. In practice, a set of catheters can be provided as in FIGS. 4A and 4B but with a number of different lengths of waist portion 14 or 14' to fit the requirements of a particular application.

Figure 5A:
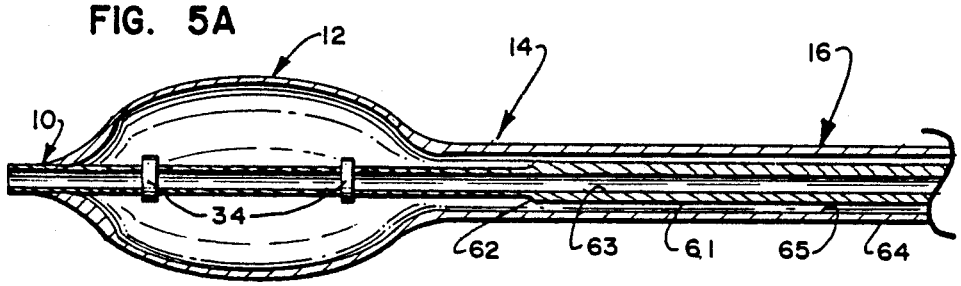
FIGS. 5A and 5B are enlarged sectional views of short and long waist catheters according to another embodiment of the invention.
Figure 5B:
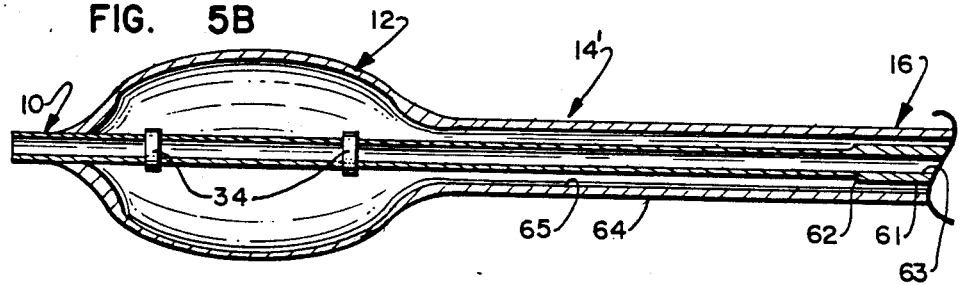

The embodiments of FIGS. 5A and 5B also use a balloon portion 14 formed integrally with the tubing which forms the outer walls of the shaft portion 16. However, in this case the variable stiffness of the waist portion 14, 14' is provided by varying the wall thickness and stiffness of the inner tube of the catheter. Specifically, the catheters of FIGS. 5A and 5B each have an inner tube 61 which changes wall thickness at zone 62, which in effect marks the transition between the relatively stiff shaft portion 16 of the catheter and the more flexible waist portion 14, 14' of the catheter. The thinner walled portion of inner tube 61 extends through the balloon portion 12 and forms the tip portion 10, and has radiopaque markers 34 as in the previous embodiments. Inner tube 61 includes central lumen 63 which receives the guide wire (not shown). Outer hollow tube 64 has an inside diameter large enough to fit over inner tube 51 and define annular lumen 65 therebetween which is used for inflating the dilatation balloon. The balloon portion 12 is formed integrally with outer tubing 64 by techniques previously discussed.

The length of the waist portion 14 between the transition zone 62 where the thickness of the inner tube 61 is reduced and the beginning of the balloon portion can be varied in length as suggested in the Figures, and a large number of different lengths can once again be provided for the surgeon to meet the needs of a particular procedure. Since the wall thickness of the inner tube 61 in the waist portion 14 is reduced, the overall stiffness of the waist portion is reduced as compared with shaft portion 16, in accordance with the invention.

Figure 6A:
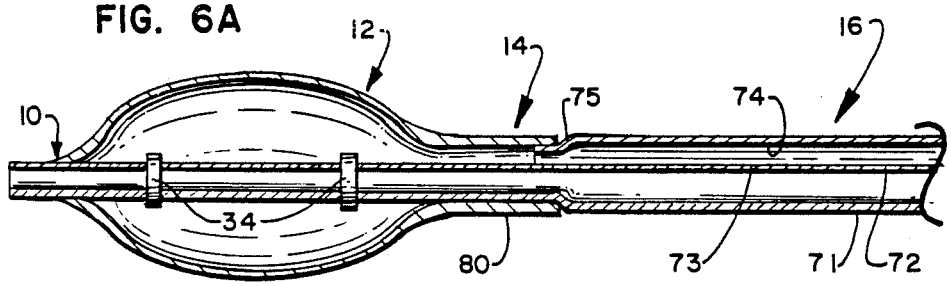
FIGS. 6A and 6B are enlarged sectional views showing short and long waist catheters according to a further embodiment of the invention.
Figure 6B:
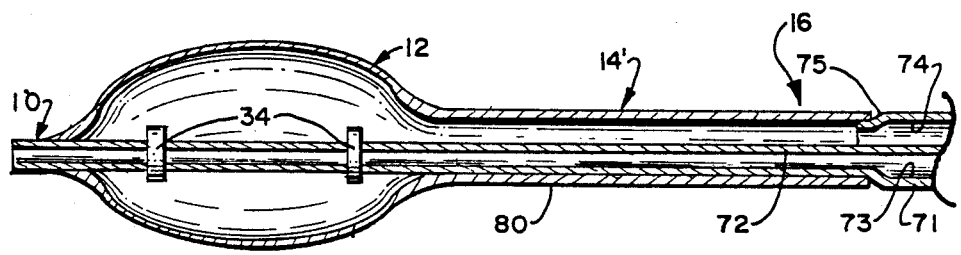

The catheters of FIGS. 6A and 6B make use of double lumen tubing for the shaft portion 16. Double lumen tubing is generally known and is used in some types of catheter construction. As seen in the sectional views the tubing includes an outer wall 71 and a central partition 72, thus defining two separate lumens 73 and 74, which are within wall 71 and separated by partition 72, and both of which extend axially through the catheter from a hub assembly (not shown) at the proximal end, to a distal end which includes the dilatation balloon. Lumen 73 is sized to receive the guide wire as the catheter is advanced. Lumen 74 is used for applying dilating pressure to the balloon. The choice of material and wall thickness for double lumen tube 71 is selected to give sufficient stiffness to transmit axial forces to advance the catheter, as previously described. At zone 75 tubing 71 is necked down somewhat so that a tube member 80 can fit over it while maintaining the approximate same outside profile to the catheter. Tubing 80 forms both the waist portion 14 and the balloon portion 12. The balloon portion 12 is formed using one of the techniques previously described.

The portion of tubing 71 above partition 72 is cut away under the waist portion 14 adjacent necked down portion 75, so that lumen 74 communicates to the interior of the balloon portion 12 for applying inflation pressure thereto. The end of tube 80 is adhesively or otherwise bonded to tubing 71 adjacent the necked down transition portion, and the distal portion of tube 80, which is the distal portion of the balloon portion, is adhesively or otherwise secured to tip 10, which is formed by partition 72 and the portion of tube 71 which was not cut away.

Since the waist portion 14 does not include the portion of tube 71 associated with inflation lumen 74, since this has been cut away, waist portion 14 will have less stiffness and greater flexibility than shaft portion 16. In FIG. 6B, the same technique of construction is used, but the waist portion 14' between balloon portion 12 and shaft portion 16 is longer. In accordance with the invention, a set or range of catheters can be provided with different incremental lengths of waist portion 14 or 14' to provide the degree of flexibility required for given applications.

Thus, the present invention provides an improved angioplasty dilatation catheter having a variable stiffness lengthwise of the catheter, and specifically providing a waist or intermediate portion behind the inflatable portion that provides maneuvering flexibility to allow the distal end to follow sharp bends in the guide wire. At the same time, the relatively stiffer shaft provides sufficient mechanical rigidity for transmitting axial force to advance the catheter, but is separated from the soft balloon portion a sufficient distance that it does not tend to push the balloon beyond sharp branches or dislodge the guide wire.

What is claimed is:

1. A coronary angioplasty dilation catheter, comprising:
   (a) an elongated flexible shaft having a distal end for entry into the vascular system and a proximal end for manipulation externally of the body and for attachment to instruments for use in a dilation procedure;
   (b) means for defining a guide wire receiving lumen, so that the catheter can be advanced along a guide wire in the vascular system of the patient;
   (c) an inflatable balloon member disposed at the distal end of the shaft;
   (d) means for fluid communication between the proximal end of said shaft and said balloon so as to provide an inflation pressure; and
   (e) means for defining a waist portion disposed between said balloon member and said shaft, said waist portion being disposed at the distal end of said shaft and being of reduced outer diameter and reduced wall thickness as compared to said shaft, the length of said waist portion between said balloon member and said shaft being equal to at least one-half of the length of said balloon member.

2. A vascular dilatation catheter according to claim 1, wherein said waist portion is made of a different material than that of said shaft.

3. A vascular dilatation catheter according to claim 2, wherein said means defining a guide wire lumen and said elongate flexible shaft comprise an elongate double lumen tubular member.

4. A coronary angioplasty dilatation catheter comprising:
   (a) an elongated tubular shaft having a distal end for entry into the vascular system and a proximal end for manipulation externally of the body and for attachment to instruments for use in a dilatation procedure;
   (b) an elongated tubular member defining a guide wire receiving lumen, disposed axially within said shaft, so that the catheter can be advanced along a guide wire in the vascular system of the patient, the distal end of said tubular member extending beyond the distal end of said shaft said tubular member having a first section and a second section, said second section disposed distally of said first section;
   (c) an inflatable balloon member disposed at the distal end of the shaft, positioned substantially coaxially over said tubular member, sealably connected at the distal end to said tubular member, and sealably connected at the proximal end to said shaft;
   (d) means for fluid communication between the proximal end of said shaft and said balloon member so as to provide an inflation pressure; and
   (e) means for defining a waist portion disposed between said balloon member and said first section of said tubular member wherein said second section of said tubular member is of reduced outer diameter and reduced wall thickness as compared to said first section of said tubular member, the length of said waist portion between said balloon member and said first section being equal to at least one-half of the length of said balloon member.

5. A vascular dilatation catheter according to claim 4, wherein said waist portion is made of a different material than that of said shaft.

6. A vascular dilatation catheter according to claim 5, wherein said tubular member and said shaft comprise an elongate double lumen tubular member.

7. A vascular dilatation catheter according to claim 1, wherein said balloon member is formed integrally with said waist portion.

8. A vascular dilatation catheter according to claim 1, wherein said waist portion is formed integrally with said shaft.

9. A vascular dilatation catheter according to claim 4, wherein said balloon member is formed integrally with said waist portion.

10. A vascular dilatation catheter according to claim 4, wherein said waist portion is formed integrally with said shaft.

11. An angioplasty dilatation catheter, comprising:
    an elongated flexible shaft having a distal end for entry into the vascular system and a proximal end for manipulation externally of the body and for attachment to instruments for use in a dilatation procedure;
    an elongated tubular member defining a guide wire receiving lumen, disposed axially within said shaft, so that the catheter can be advanced along a guide wire in the vascular system of the patient;
    an inflatable balloon member disposed at the distal end of the shaft, positioned substantially coaxially over said tubular member, sealably connected at the distal end to said tubular member;
    means for fluid communication between the proximal end of the shaft and said balloon member; and
    means for defining a waist portion formed integrally with said balloon member and disposed at the distal end of said shaft between said shaft and said balloon member, said waist portion being of reduced outer diameter and reduced wall thickness as compared to said shaft, the length of said waist portion between said balloon member and said shaft being equal to at least one-half of the length of said balloon member.

12. The angioplasty dilatation catheter of claim 11 wherein the waist portion and said balloon member are made of a material comprising a polyolefin.

13. The angioplasty dilatation catheter of claim 12 wherein said polyolefin comprises a polyethylene.

14. The angioplasty dilatation catheter of claim 11 further including at least one radiopaque marker disposed within said balloon member.

15. The angioplasty dilatation catheter of claim 11 further including a tip member extending distally from said balloon member, said tip member being more flexible than said balloon member.

16. The angioplasty dilatation catheter of claim 15 wherein said tip member comprises a length of said annular tubular member extending distally of said balloon member.

17. The angioplasty dilatation catheter of claim 11 wherein said shaft is formed integrally with said waist portion.

18. An angioplasty dilatation catheter, comprising:
    an elongated flexible main shaft having a distal end for entry into the vascular system and a proximal end for manipulation externally of the body and for attachment to instruments for use in a dilatation procedure;

an elongated tubular member defining a guide wire receiving lumen, disposed axially within said shaft, so that the catheter can be advanced along a guide wire in the vascular system of the patient;

an inflatable balloon member;

means for fluid communication between the proximal end of the main shaft and said balloon member so as to provide an inflation pressure; and a waist portion shaft disposed between said balloon member and said main shaft, the distal end of said waist portion shaft being formed integrally with said balloon member and the proximal end of said waist portion shaft being bonded to the distal end of said main shaft, said waist portion shaft being of reduced outer diameter and reduced wall thickness as compared to said main shaft, the length of said waist portion shaft between said balloon member and said main shaft being equal to at least one-half the length of said balloon member.

19. The angioplasty dilatation catheter of claim 18 wherein said waist portion shaft and said balloon member are made of a material comprising a polyolefin.

20. The angioplasty dilatation catheter of claim 19 wherein said polyolefin comprises a polyethylene.

21. The angioplasty dilatation catheter of claim 18 further including at least one radiopaque marker disposed within said balloon member.

22. The angioplasty dilatation catheter of claim 18 further including a tip member extending distally from said balloon member, said tip member being more flexible than said balloon member.

23. The angioplasty dilatation catheter of claim 22 wherein said tip member comprises a length of said annular tubular member extending distally of said balloon member.

24. An angioplasty dilatation catheter, comprising:

an elongated flexible main shaft having a distal end for entry into the vascular system and a proximal end for manipulation externally of the body and for attachment to instruments for use in a dilatation procedure;

an elongated tubular member defining a guide wire receiving lumen, disposed axially within said shaft, so that the catheter can be advanced along a guide wire in the vascular system of the patient;

an inflatable balloon member, positioned substantially coaxially over said tubular member, sealably connected at the distal end to said tubular member;

a tip member extending distally from said balloon member, said tip member being more flexible than said balloon member;

a waist portion shaft disposed substantially coaxially over said tubular shaft member between said balloon member and said main shaft, the distal end of said waist portion shaft being formed integrally with said balloon member and the proximal end of said waist portion shaft being bonded to the distal end of said main shaft, said waist portion shaft being made of a different material than said main shaft and being of reduced outer diameter and reduced wall thickness as compared to said main shaft, the length of said waist portion shaft between said balloon member and said main shaft being equal to at least one-half of the length of said balloon member; and an annular lumen being defined through said tubular shaft, said main shaft and said waist portion shaft, said annular lumen providing fluid communication between the proximal end of said main shaft and said balloon member so as to provide an inflation pressure.

25. The angioplasty dilatation catheter of claim 24 wherein said waist portion shaft and said balloon member are made of a material comprising a polyolefin.

26. The angioplasty dilatation catheter of claim 25 wherein said polyolefin comprises a polyethylene.

27. The angioplasty dilatation catheter of claim 24 further including at least one radiopaque marker disposed within said balloon member.

28. The angioplasty dilatation catheter of claim 25 further including at least one radiopaque marker disposed within said balloon member.

29. A coronary angioplasty dilatation catheter, comprising:

(a) an elongated flexible shaft having a distal end for entry into the vascular system and a proximal end for manipulation externally of the body and for attachment to instruments for use in a dilatation procedure;

(b) means for defining a guide wire receiving lumen, so that the catheter can be advanced along a guide wire in the vascular system of the patient;

(c) an inflatable balloon member disposed at the distal end of the shaft;

(d) means for fluid communication between the proximal end of said shaft and said balloon so as to provide an inflation pressure; and (e) means for defining a waist portion disposed between said balloon member and said shaft, said waist portion being disposed at the distal end of said shaft and being of reduced outer diameter and reduced wall thickness as compared to said shaft, the length of said waist portion between said balloon member and said shaft being equal to at least one length of said balloon member.

30. A coronary angioplasty dilatation catheter, comprising:

(a) an elongated tubular shaft having a distal end for entry into the vascular system and a proximal end for manipulation externally of the body and for attachment to instruments for use in a dilatation procedure;

(b) an elongated tubular member defining a guide wire receiving lumen, disposed axially within said shaft, so that the catheter can be advanced along a guide wire in the vascular system of the patient, the distal end of said tubular member extending beyond the distal end of said shaft said tubular member having a first section and a second section, said second section disposed distally of said first section;

(c) an inflatable balloon member disposed at the distal end of the shaft, positioned substantially coaxially over said tubular member, sealably connected at the distal end to said tubular member, and sealably connected at the proximal end to said shaft;

(d) means for fluid communication between the proximal end of said shaft and said balloon member so as to provide an inflation pressure; and (e) means for defining a waist portion disposed between said balloon member and said first section of said tubular member wherein said second section of said tubular member is of reduced outer diameter and reduced wall thickness as compared to said first section of said tubular member, the length of said waist portion between said balloon member and said first section being equal to at least one length of said balloon member.

31. An angioplasty dilatation catheter, comprising:

an elongated flexible main shaft having a distal end for entry into the vascular system and a proximal end for manipulation externally of the body and for attachment to instruments for use in a dilatation procedure;

an elongated tubular member defining a guide wire receiving lumen, disposed axially within said shaft, so that the catheter can be advanced along a guide wire in the vascular system of the patient;

an inflatable balloon member;

means for fluid communication between the proximal end of the main shaft and said balloon member so as to provide an inflation pressure; and a waist portion shaft disposed between said balloon member and said main shaft, the distal end of said waist portion shaft being formed integrally with said balloon member and the proximal end of said waist portion shaft being bonded to the distal end of said main shaft, said waist portion shaft being of reduced outer diameter and reduced wall thickness as compared to said main shaft, the length of said waist portion shaft between said balloon member and said main shaft being equal to at least one length of said balloon member.

32. An angioplasty dilatation catheter, comprising:

an elongated flexible main shaft having a distal end for entry into the vascular system and a proximal end for manipulation externally of the body and for attachment to instruments for use in a dilatation procedure;

an elongated tubular member defining a guide wire receiving lumen, disposed axially within said shaft, so that the catheter can be advanced along a guide wire in the vascular system of the patient;

an inflatable balloon member, positioned substantially coaxially over said tubular member, sealably connected at the distal end to said tubular member;

a tip member extending distally from said balloon member, said tip member being more flexible than said balloon member;

a waist portion shaft disposed substantially coaxially over said tubular shaft member between said balloon member and said main shaft, the distal end of said waist portion shaft being formed integrally with said balloon member and the proximal end of said waist portion shaft being bonded to the distal end of said main shaft, said waist portion shaft being made of a different material than said main shaft and being of reduced outer diameter and reduced wall thickness as compared to said main shaft, the length of said waist portion shaft between said balloon member and said main shaft being equal to at least one length of said balloon member; and an annular lumen being defined through said tubular shaft, said main shaft and said waist portion shaft, said annular lumen providing fluid communication between the proximal end of said main shaft and said balloon member so as to provide an inflation pressure.

* * * * *

Disclaimer 4,976,690—Ronald J. Solar, Minnetonka; and Jonathan Kagan, Minneapolis, both of Minn. VARIABLE STIFFNESS ANGIOPLASTY CATHETER. Patent dated Dec. 11, 1990. Disclaimer filed Oct. 7, 1998, by the assignee, SciMed Life Systems, Inc.

Hereby enters this disclaimer to claims 3 and 6 of said patent.

*(Official Gazette, November 17, 1998)*